United States Patent
Pougatchev et al.

(10) Patent No.: US 6,305,943 B1
(45) Date of Patent: Oct. 23, 2001

(54) RESPIRATORY SINUS ARRHYTHMIA TRAINING SYSTEM

(75) Inventors: Vadim I. Pougatchev; Eugene N. Zhirnov; Eugene N. Gribkov, all of Gig Harbor, WA (US)

(73) Assignee: Biomed USA, Inc., Poulsbo, WA (US)

( * ) Notice: Subject to any disclaimer, the term of this patent is extended or adjusted under 35 U.S.C. 154(b) by 0 days.

(21) Appl. No.: 09/494,254

(22) Filed: Jan. 28, 2000

Related U.S. Application Data

(60) Provisional application No. 60/117,969, filed on Jan. 29, 1999.

(51) Int. Cl.[7] ................................................. G09B 23/28
(52) U.S. Cl. .......................... 434/262; 434/238; 434/247; 434/265; 600/300; 600/529
(58) Field of Search ..................... 434/236–238, 434/247, 262, 265, 307 R, 308, 365; 600/21, 27, 300, 484, 509, 515, 523, 529, 532–534, 538, 544–547; 602/42; 607/46, 48; 704/207, 209, 270

(56) References Cited

U.S. PATENT DOCUMENTS

| | | | |
|---|---|---|---|
| 5,027,824 | * | 7/1991 | Dougherty et al. ............... 600/515 |
| 5,520,192 | * | 5/1996 | Kitney et al. ..................... 600/529 |
| 5,694,939 | * | 12/1997 | Cowings ............................ 600/484 |
| 5,701,894 | * | 12/1997 | Cherry et al. ..................... 600/300 |
| 5,725,472 | * | 3/1998 | Weathers ............................ 600/21 |
| 5,944,680 | * | 8/1999 | Christopherson .................. 602/42 |
| 6,024,699 | * | 2/2000 | Surwit et al.l. ................... 600/300 |
| 6,026,322 | * | 2/2000 | Korenman et al. ................ 600/547 |

\* cited by examiner

Primary Examiner—Joe H. Cheng
(74) Attorney, Agent, or Firm—Johnson & Stainbrook, LLP; Larry D. Johnson; Craig M. Stainbrook

(57) ABSTRACT

A biofeedback training method and apparatus to increase and reinforce the respiratory sinus arrhythmia as an outcome of a breath training technique, said apparatus comprising a physiological monitoring device that provides raw physiological data to a computer having a software program that receives and utilizes the heartbeat interbeat interval information supplied by the physiological sensors, calculates such intervals after every heartbeat, computes RSA parameters from the interbeat intervals, displays raw signal instantaneous heart rate values, calculates RSA parameters in the form of graphs, compares current values of the RSA training score with currently set threshold level to generate training feedback, provides continuous audiovisual feedback to the user to reward training attempts based on results of threshold comparisons, displays a breath pacer to induce an appropriate breathing pattern, recommended by selected breathing technique, saves interbeat intervals along with the RSA parameters into a built-in database for further review of training sessions, and permits the user to make several adjustments.

18 Claims, 4 Drawing Sheets

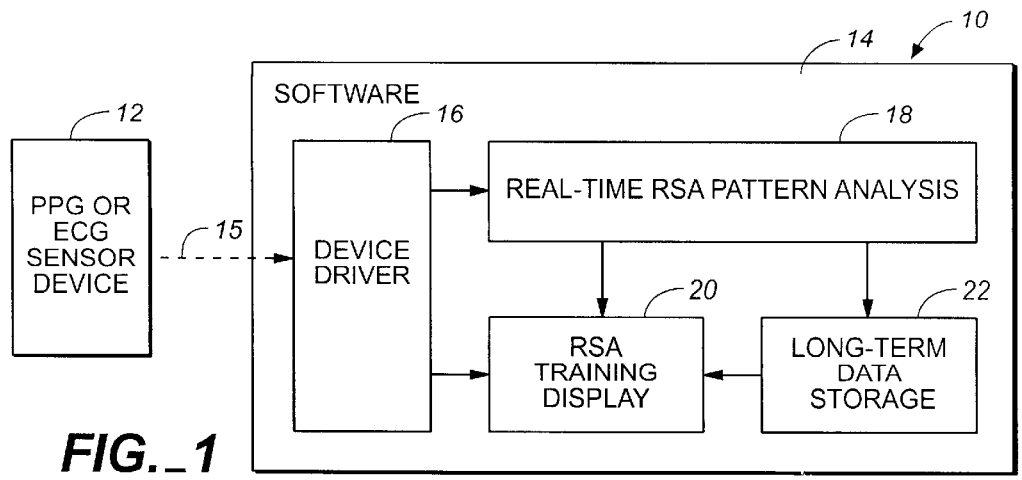
FIG._1
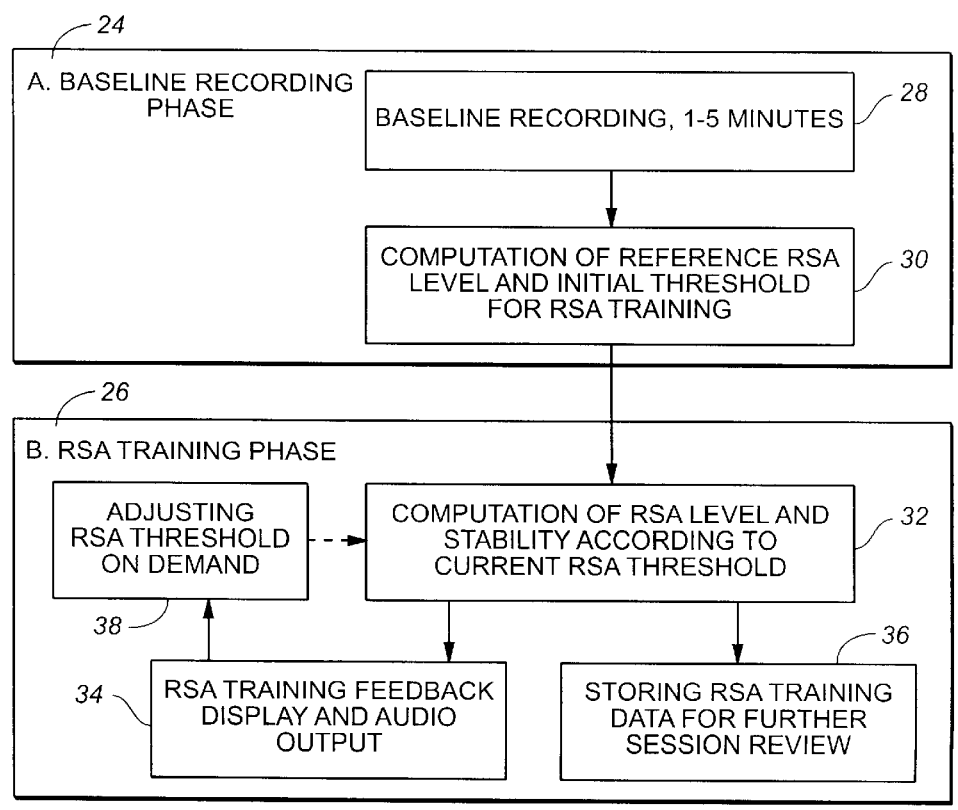
FIG._2

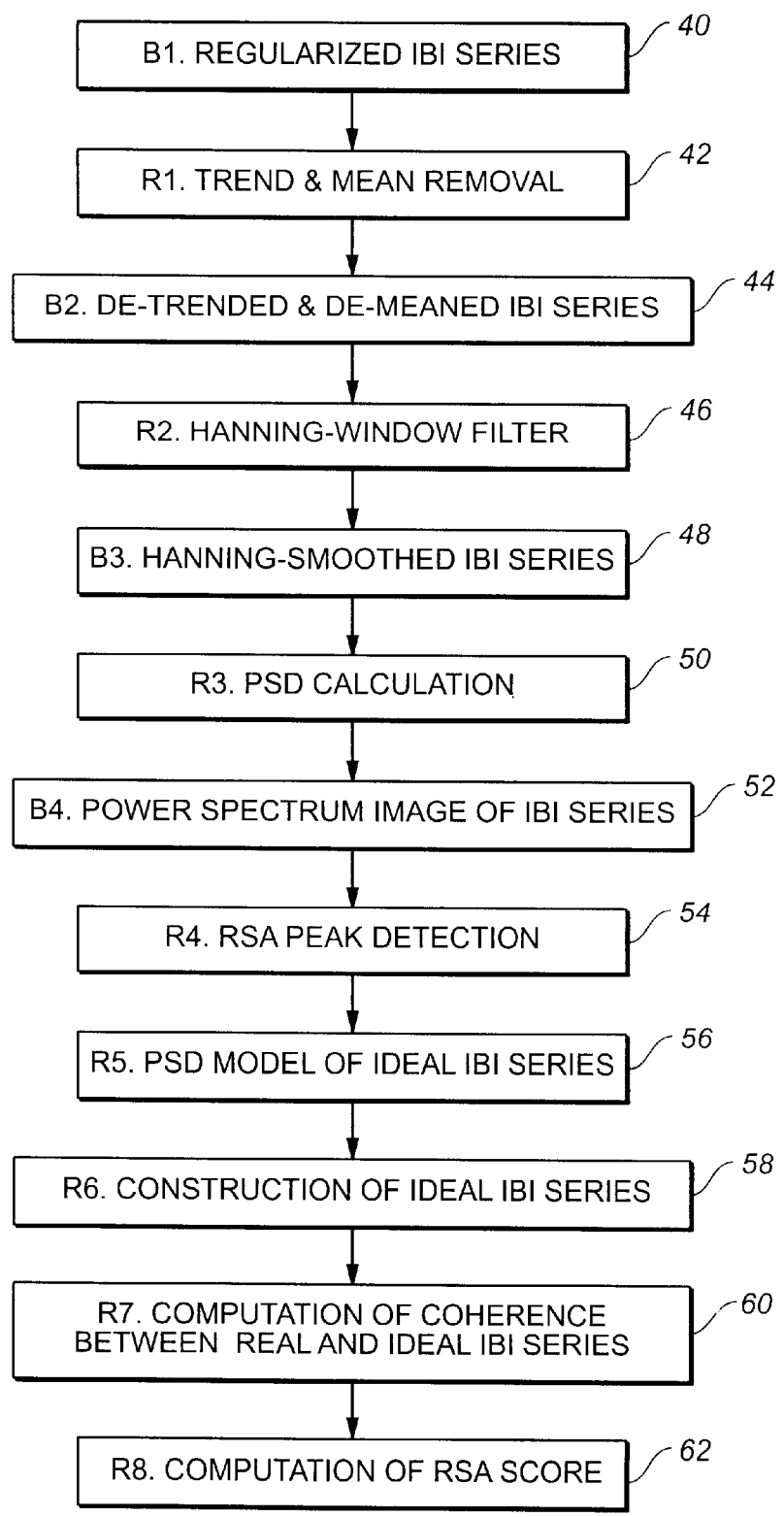
FIG._3

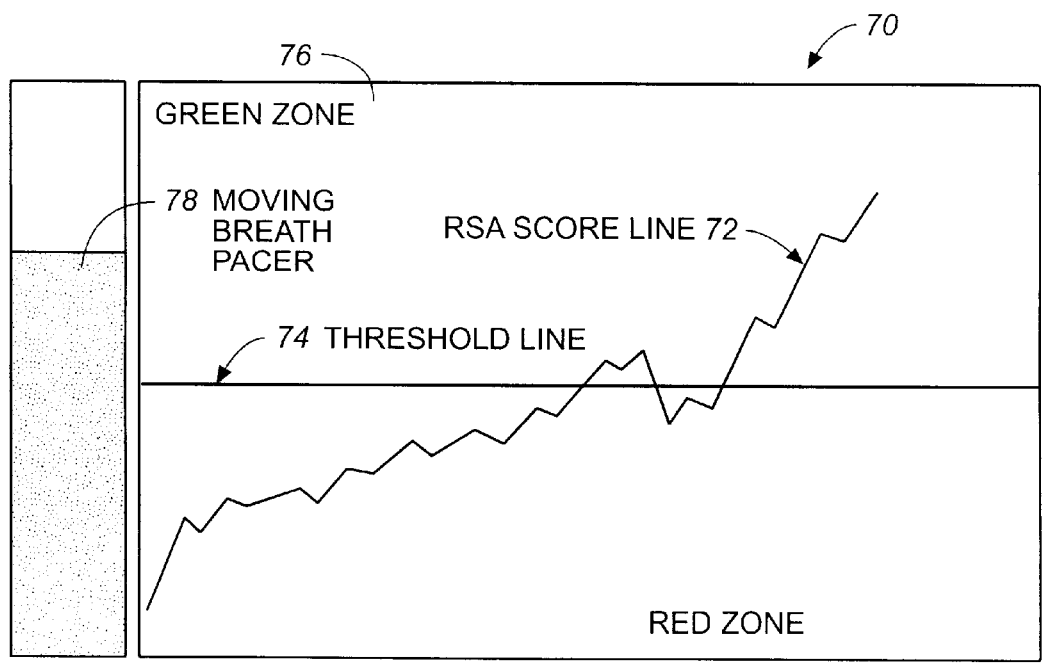
FIG._4
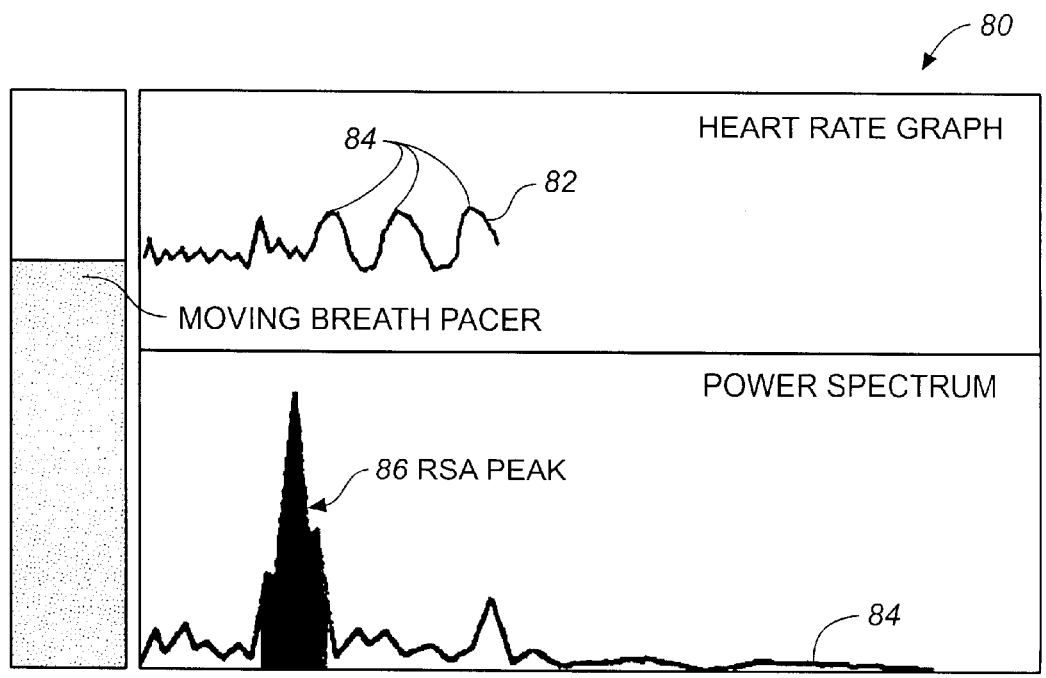
FIG._5

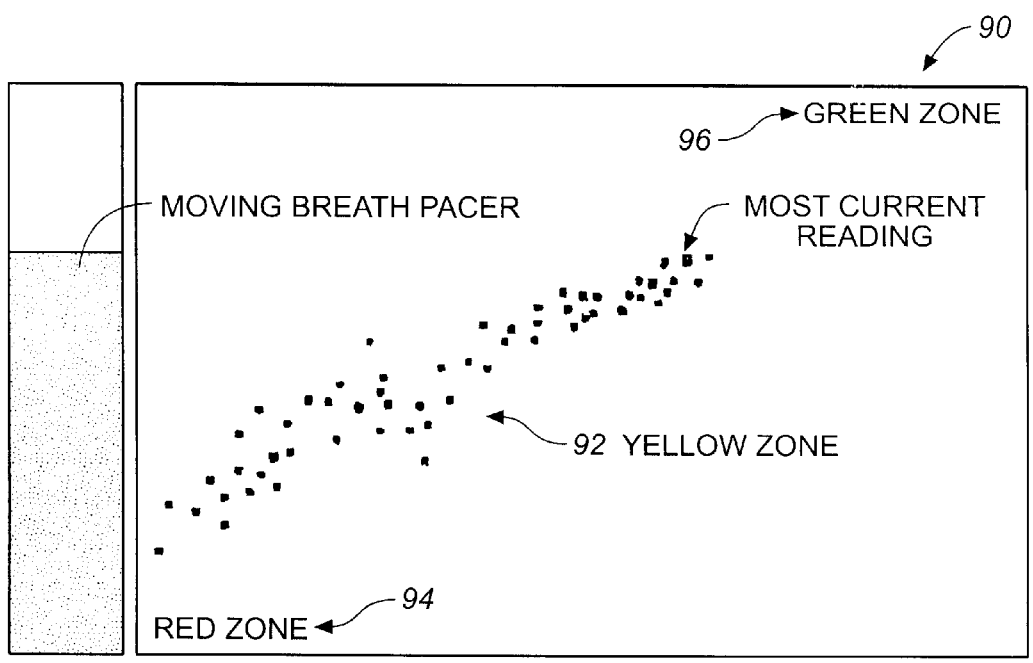
FIG._6
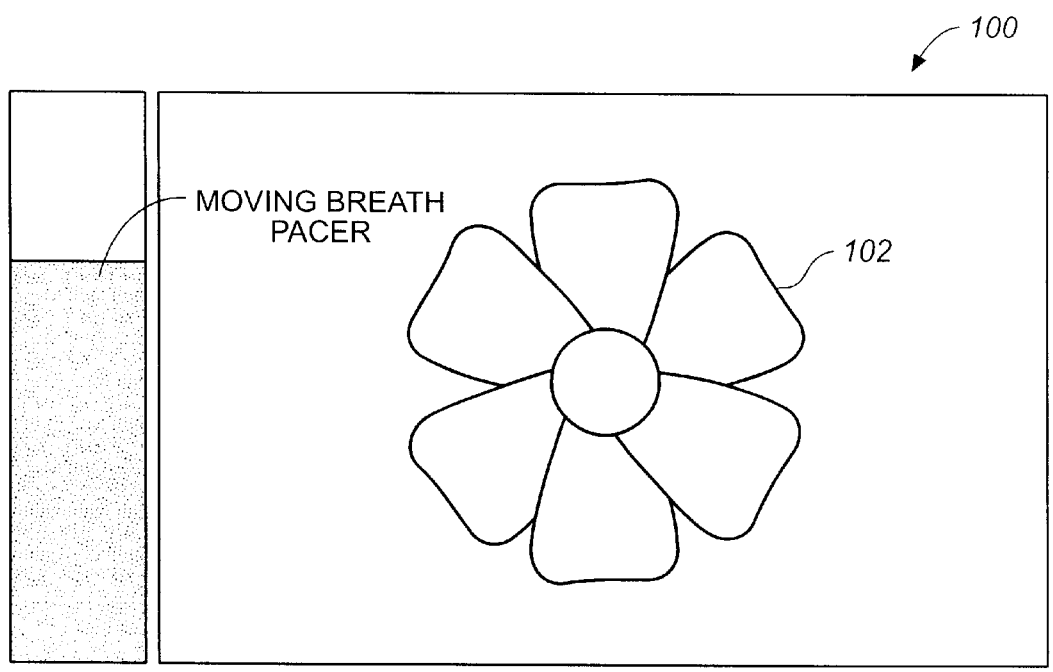
FIG._7

RESPIRATORY SINUS ARRHYTHMIA TRAINING SYSTEM

CROSS REFERENCE TO RELATED APPLICATIONS

The present application claims the benefit of the filing date of U.S. Provisional Application, Ser. No. 60/117,969, filed Jan. 29, 1999.

BACKGROUND OF THE INVENTION

1. Field of the Invention

This invention relates generally to breath training techniques, and more particularly to an apparatus and method for monitoring the respiratory sinus arrhythmia as a biofeedback tool during various breathing training techniques.

2. Description of Related Art

It is known that the autonomic nervous system (ANS) regulatory mechanism has an influence on various organs and systems of the human body. The system works as a highly complex set of interacting physiological oscillators. One of the main functions of the ANS is to maintain an optimum balance between those oscillators. Any prolonged regulatory imbalance may cause functional disorders eventually debilitating the entire human organism. One of the major causes of such imbalance is psycho-emotional stress. There are many techniques that claim a means for stress reduction, which provides a positive effect on the ANS regulatory function. The goal of such techniques is to switch the ANS into a specific "resonant" state characterized by a synchronous, smooth, coherent, sine-like pattern of oscillations of many physiological parameters, e.g. heart rate (HRT), blood pressure (BP), breathing rate (BR), pulse wave propagation time (PWPT), and so forth.

A good example of resonant state phenomena is the respiratory sinus arrhythmia pattern (RSA), where HRT is oscillating synchronously to the breathing cycle. Since one of the goals of stress reduction techniques is to increase the resonance between oscillating physiological parameters, it is important to be able to dynamically evaluate a quantitative measure of the significance and stability of the resonant pattern and establish feedback to reinforce the positive changes.

Some key facts are worth noting:
1. There are numerous well-known breathing techniques used in clinical rehabilitation, stress management, sports and fitness training, alternative medicine and Yoga, etc.
2. The positive effect of breathing exercises is related to the influence of breathing on the sympato-vagal neuro-regulation of cardiovascular system. Two branches of the autonomic nervous system (sympathetic and parasympathetic) have their antagonistic effects on the heart, blood vessels and all other systems and organs of the human body. One of the predicates of well being is to learn how to maintain an optimal balance between these two branches of the regulatory mechanism.
3. Heart rate variability (HRV) has been recognized as a key marker that reflects the condition of both the sympathetic and parasympathetic nervous systems and their balance. HRV indicates how the time between consecutive heartbeats (interbeat intervals) varies. This variability has a direct effect on the two branches of autonomic nervous regulation.
4. It has been noted and supported by numerous research studies that breathing causes a specific pattern of heart rate variability called respiratory sinus arrhythmia (RSA). Normal breathing has a fairly stable pattern described by respiration rate, volume of breathing, lengths of all components of breath cycle (inhalation, exhalation, pauses at the end of inhalation and exhalation). The RSA effect produces a pattern of variations of heartbeats synchronous to the breath cycles.
5. Normal (tidal) breathing causes noticeable RSA patterns in relatively healthy human subjects. Its significance is decreased with age, conditions of stress, depression, panic, anxiety and many other functional and psychosomatic disorders.
6. Various breathing exercises that alter breath patterns increase the significance of the RSA pattern. This effect is considered as a reflection of the healing mechanism of the breathing exercise, which causes a positive influence or harmonization of both the sympathetic and parasympathetic nervous regulation.
7. Providing subjects with the means to maintain a specific breathing pattern results in an increase of the RSA effect followed by positive changes in HRV parameters. This change is a direct indicator of the normalization of sympato-vagal regulation of the overall organism.

To conduct HRV analysis and particularly evaluate the RSA pattern an electrocardiograph (ECG) signal is usually measured. The interbeat intervals are derived from the ECG as the intervals between consecutive R-peaks. This method is very accurate and reliable but has a significant disadvantage: namely, it requires the use of complex and expensive ECG equipment with multiple electrode placements on the wrists or the chest. An alternative is to use a photoplethysmograph (PPG) measurement by means of a portable and convenient finger sensor. The PPG sensor emits an infrared (IR) light on the skin. The emitted light is partially consumed by the blood flow. The degree of light consumption/reflection is proportional to the changes in blood flow. The PPG signal has periodic peaks that represent blood vessel pulsation. It can be also used to derive the interbeat intervals representing the time between two PPG peaks.

SUMMARY OF THE INVENTION

The present invention comprises a biofeedback training method and apparatus that establishes and reinforces the increase of the respiratory sinus arrhythmia as an outcome of the breathing technique setup. The hardware of the apparatus comprises a physiological monitoring device, such as an EEG or PPG sensor, that provides raw physiological data to a computer having a specifically designed computer software program that carries out the critical computations underlying the method of the present invention. It is assumed that such computer software program utilizes the interbeat interval information supplied by an ECG or PPG sensors, for example, and calculates such intervals after every heartbeat. Thus the current invention is indifferent to the source of interbeat interval information.

The software carries out the following functions:
(A) In Real-time it Continuously Receives interbeat intervals along with raw signal (ECG or PPG) from dedicated device by means of specific device driver;

Computes RSA parameters (RSA Training Score and RSA Training Stability) from the interbeat intervals using a proprietary algorithm that will be described below;

Displays raw signal (ECG or PPG), cardiotachogram (instantaneous values of heart rate) and calculated RSA parameters in the form of graphs;

Compares current values of the RSA Training Score with currently set threshold level to generate training feedback;

Provides continuous audio-visual feedback to the user to reward training attempts based on results of threshold comparisons;

Displays a breath pacer to induce an appropriate breathing pattern, recommended by selected breathing technique;

Saves interbeat intervals along with the RSA parameters into a built-in database for further review of training session.

(B) At Any Time on the User's Demand the Following Adjustments are Available:

Adjusts RSA training score threshold for better training feedback during training session;

Adjusts parameters of the breath pacer pattern for better breathing technique compliance;

Displays achieved results of the selected RSA training session (Session Summary);

Displays achieved results of the RSA training across all recorded sessions (Progress Summary);

Prints RSA training reports of pre-designed format.

BRIEF DESCRIPTION OF THE DRAWINGS

FIG. 1 is a block diagram illustrating the functional scheme of the respiratory sinus arrhythmia training system of the present invention;

FIG. 2 illustrates a structure of the RSA training protocol;

FIG. 3 illustrates the algorithm of the evaluation of the RSA training score;

FIG. 4 illustrates the main RSA training screen, where the RSA score is displayed in the form of line graph with current threshold shown as a horizontal line;

FIG. 5 illustrates another possible RSA training screen showing a time series of interbeat intervals (cardiotachogram) along with the power spectrum graph of this time series;

FIG. 6 illustrates another possible RSA training screen that displays actual RSA score and RSA stability values in the form of X-Y scatter graph, where X -scale represents RSA stability and Y-scale-RSA score; and FIG. 7 illustrates an animated image training screen as an alternative visual display for ongoing RSA training.

DETAILED DESCRIPTION OF A PREFERRED EMBODIMENT

FIG. 1 illustrates the functional scheme of the respiratory sinus arrhythmia training system 10 of the present invention. A physiological monitoring device 12, preferably either an ECG or PPG sensor, transmits both raw signal (ECG or PPG) and interbeat interval (IBI) sequence to a computer 14 through a standard interface 15, preferably a standard serial interface, but including an RS232, USB, infrared or RF device. When the apparatus is in its operational mode and a subject is appropriately connected to the physiological monitoring device, a device driver 16 gathers transmitted information in real-time mode and keeps it in its internal buffer. The software program provides a real-time analysis of the IBI series 18 by means of applying a special algorithm of computation of the RSA parameters reflecting the current RSA pattern. It also transfers the gathered data (raw signal along with IBI) and result of the RSA analysis to its presentation module 20 for live data display. The software stores the results of analysis in its long-term storage 22 (built-in database). This feature allows for the reviewing of the RSA data any time after the monitoring session is finished.

FIG. 2 illustrates a structure of the RSA training protocol. The protocol consists of two phases: (A) a baseline recording phase 24 and (B) an RSA training phase 26. During the baseline recording 28 an interbeat interval time series of a certain length is collected. Then an initial RSA training score is evaluated 30. This score reflects the significance of the natural RSA phenomena not caused by a specific breathing exercise. As is known, the human subject might have a spontaneous RSA at a noticeable level. Thus, the initial RSA score is used as a reference point to establish an initial threshold level of RSA for further training. This allows for a very individualized automatic threshold selection provided for training simplicity and effectiveness. The baseline data is also used to evaluate a startup rate for a breath pacer used to induce an RSA pattern. In case of the presence of a natural RSA the interbeat interval data is used to estimate the current respiration rate. Such rate is used to set a startup breath pacer rate avoiding a rapid change in breathing rate when starting a breathing exercise. If the natural RSA pattern is not noticeable and the algorithm cannot reliably pick up a respiration rate out of baseline data, a predetermined respiration rate is applied to the breath pacer at the training startup.

During the RSA training phase 26, the length of which is set up by the user, the program repetitively computes the current RSA Training Score and RSA Training Stability 32. The RSA training stability means the percent of the training time when the RSA score is above the current threshold level. These two parameters are used for the evaluation of the RSA training success because the system's two objectives are: (a) to achieve the highest RSA score by the end of training phase; and (b) to maintain RSA score above threshold as long as possible during the training. When the new RSA parameters are computed, the system displays them in various types of graphical presentation and generates auditory and/or visual feedback 34 when RSA score is above threshold. It also stores the computed parameters in built-in database 36 for further review of the Session or Progress Summary. To increase or decrease the challenge of the ongoing training, the user can manually set an RSA score threshold 38 at any time and level.

At any time the rate of the present breath pacer (described, infra) can be changed as well. This helps to avoid discomfort caused by too low or high of a breath pace that was previously set to facilitate the higher RSA effect. When the training session is accomplished a session report can be displayed that presents the training achievement results.

The present invention applies an algorithm for the quantitative evaluation of physiological oscillation pattern and its proximity to the "ideal" coherent rhythm as a means to determine the RSA pattern significance. This algorithm employs an assumption that true RSA pattern has a distinct sine-like nature. The ideal pattern assumes a pure sine-like oscillation of interbeat intervals with the same basic statistical characteristics. The algorithm computes a special parameter called RSA Training Score that quantitatively indicates how close the current RSA pattern is to the sine-like one. It is measured in a percentage scale, where zero percent (0%) means an irregular (close to "white noise") heart rhythm, and one hundred percent (100%) means a highly synchronized (close to sine) rhythm.

FIG. 3 illustrates the algorithm of the evaluation of the RSA training score. The following summarizes the sequence of steps representing this algorithm:

1. Collect a series of samples of the interbeat intervals (at least 256 samples, 2 samples per second) measured in milliseconds;
2. Condition a series of samples: trend removal, mean removal, convolution of a series with a wide Hamming or Hanning window to eliminate "edge effect" of the series;

3. Calculate an FFT image of the sampled series;
4. Find a maximum peak on FFT in the range of frequencies where a dominant peak is expected. The range of frequencies is automatically calculated based on currently set breath pacer rate;
5. Calculate a convolution of the FFT image with an exponential type window centered at a found peak frequency to create an FFT of the "ideal" model signal for comparison;
6. Calculate model series of samples from the model FFT by means of inverse FFT procedure;
7. Condition a model series (similar to step 2);
8. Calculate a coherence function between the original and modeled series. Both series must be conditioned as described above; and
9. Calculate an integral of the coherence function as a scalar parameter and convert it into percent value (multiplying value by 100).

The regularized interbeat intervals 40 (oversampled at certain rate) kept in a respective buffer B1 are processed by R1 routine 42 that removes trend and mean value out of this series. The result 44 is in buffer B2. It is used by R2 routine that applies a Hanning window filtering procedure 46 to eliminate boundary effects of the series of limited size. Filtered series 48 is placed to the buffer B3, which is used by R3 routine 50 to compute a power spectrum density (PSD) 52 of this series placed into B4 buffer. Then R4 procedure 54 finds a maximum peak of the power spectrum in the range of frequencies where RSA peak is expected. This frequency range is determined by the rate of breathing induced by breath pacer. R5 and R6 procedures, 56 and 58, respectively, create a model of "ideal" series of interbeat intervals that is a sine-like periodic signal matching to real one in basic statistics. They both must have matching peak frequency and integral of power spectrum in the range of peak frequency +/−0.05 Hz. First, an "ideal" PSD is generated, then an "ideal" IBI series is calculated by means of the inverted PSD calculation procedure. R7 procedure 60 computes a mathematical coherence function between real and "ideal" IBI series. This function reflects a measure of similarity of these two processes for each frequency. If the real series has a distinctive RSA wave, the coherence function would produce values close to 1 in the range close to peak frequency and close to zero in other frequency ranges. Finally R8 procedure 62 calculates RSA Training Score parameter. It is an average of all values of coherence function in the range of frequencies from 0.0033 Hz to 0.4 Hz. When an RSA score threshold of certain level is applied, the RSA Stability parameter is being calculated. It represents a relative time of training when RSA score is above threshold level. Said threshold level is automatically determined as a reference RSA level computer during baseline phase.

Another important aspect of the RSA training method is an appropriate visual presentation of the RSA data (both RSA score and stability) during the training. This presentation should have a rapid response time and provide the obvious and intuitive perception to be able to create a feedback loop.

FIG. 4 illustrates the main RSA training screen 70, where the RSA score 70 is displayed in the form of line graph with current threshold shown as a horizontal line 72. The plot surface is preferably painted in two colors: e.g., pale green above threshold line and pale red below threshold line. Such an intuitively obvious display shows the zone of success, in this instance the green zone 74. The program continuously displays suggested breath pacer as a vertical bar 76, to which the trainee should synchronize his/her breathing.

FIG. 5 illustrates another possible RSA training screen 80 that demonstrates a time series of interbeat intervals (cardiotachogram) 82 along with the power spectrum graph of this time series. When a good RSA pattern is developed it is seen on cardiotachogram as a smooth and coherent wave pattern 84. At the same time a power spectrum graph shows a significant peak in the range of frequencies where RSA peak 86 is expected in accordance with maintained respiration rate. This frequency range is highlighted by the color on the power spectrum graph.

FIG. 6 illustrates yet another possible RSA training screen 90 that displays actual RSA score and RSA stability values in the form of X-Y scatter graph 92, where X-scale represents RSA stability and Y-scale-RSA score. The plot surface is preferably painted with a color gradient smoothly transformed from pale red in lower left corner 94 to pale green in upper right corner 96. Each new set of these two parameters is displayed as a new dot on this graph. In the course of time the color of each dot becomes more and more dark as soon as those values become older in a time series. The color gradient of the plot surface also intuitively guides the trainee to the zone of success, providing an immediate visual feedback.

FIG. 7 illustrates one more possible type of visual display 100 of ongoing RSA training. It provides animation of the image, like simple cartoon. Each particular cartoon frame is related to a specific value (or range of values) of the RSA score. As the RSA score becomes higher or lower the screen image is immediately updated to show intuitively obvious positive or negative progress. As an example, there is a flower 102 that can grow on the screen as the RSA score gets higher.

The method of using the foregoing hardware and software entails the selection of an appropriate breath training technique, providing the operational apparatus as described above, fastening the physiological monitoring device so as to acquire raw physiological data from the subject, and beginning the feedback program.

What is claimed as invention is:
1. An apparatus for monitoring respiratory sinus arrhythmia as a feedback tool in a breath training session, said apparatus having an operational mode and comprising:
 a computer;
 a visual display screen;
 at least one physiological monitoring device selected from the group consisting of electrocardiogram (ECG) and photoplethysmograph (PPG) sensors for transmitting raw physiological data to said computer, said raw physiological data including interbeat interval data;
 means for transmitting the raw physiological data from said physiological monitoring device to said computer;
 a device driver for receiving the interbeat interval data along with raw physiological date signals from said at least one physiological monitoring device; and
 a software program installed on said computer that utilizes the interbeat interval information supplied by said physiological monitoring device and calculates such intervals after every heartbeat, and further performs the following operations:
  (a) computes RSA parameters, including RSA Training Score and RSA Training Stability, from the interbeat intervals;
  (b) visually displays raw signal instantaneous values of heart rate and calculated RSA parameters in the form of graphs;
  (c) compares current values of the RSA Training Score with a currently set threshold level to generate training feedback;

(d) provides continuous audio-visual feedback to the user to reward training attempts based on results of threshold comparisons, said feedback including a least an RSA score; and (e) visually displays a breath pacer to induce an appropriate breathing pattern in the user as recommended by the selected breathing technique.

2. The apparatus of claim 1 wherein said software includes a built-in database and further saves interbeat intervals along with the RSA parameters into the built-in database for future review of the breath training session.

3. The apparatus of claim 1 further including means whereby at any time on the user's demand the user may adjust RSA training score threshold for better training feedback during training session.

4. The apparatus of claim 1 further including means whereby at any time on the user's demand the user may adjust parameters of the breath pacer pattern for better breathing technique compliance.

5. The apparatus of claim 1 wherein said software further displays a session summary showing the results of the selected RSA training session.

6. The apparatus of claim 1 wherein said software further displays a progress summary showing the results of the RSA training across all recorded sessions.

7. The apparatus of claim 1 wherein said software further provides printed RSA training reports.

8. The apparatus of claim 1 wherein said physiological monitoring device is an ECG.

9. The apparatus of claim 1 wherein said physiological monitoring device is a PPG.

10. A method of monitoring respiratory sinus arrhythmia as a feedback tool in a breath training session, said method comprising the steps of:

providing a computer, a visual display screen, at least one physiological monitoring device selected from the group consisting of electrocardiogram (ECG) and photoplethysmograph (PPG) sensors for transmitting raw physiological data to said computer, said raw physiological data including interbeat interval data, means for transmitting the raw physiological data from said physiological monitoring device to said computer, a device driver for receiving the interbeat interval data along with raw physiological date signals from said at least one physiological monitoring device, and a software program installed on said computer that utilizes the interbeat interval information supplied by said physiological monitoring device and calculates such intervals after every heartbeat, said software program further performing the following operations:

(a) computation of RSA parameters, including RSA Training Score and RSA Training Stability, from the interbeat intervals;

(b) visual display of raw signal instantaneous values of heart rate and calculated RSA parameters in the form of graphs;

(c) comparison of current values of the RSA Training Score with a currently set threshold level to generate training feedback;

(d) provision of continuous audio-visual feedback to the user to reward training attempts based on results of threshold comparisons, said feedback including a least an RSA score; and (e) visual displays of a breath pacer to induce an appropriate breathing pattern in the user as recommended by the selected breathing technique;

selecting an appropriate breath training technique for the user;

connecting said physiological monitoring device to said user so as to acquire and transmit said raw physiological data; and placing the apparatus in its operational mode.

11. The method of claim 10 wherein said software includes a built-in database and further saves interbeat intervals along with the RSA parameters into the built-in database for future review of the breath training session.

12. The method of claim 10 further including means whereby at any time on the user's demand the user may adjust RSA training score threshold for better training feedback during training session.

13. The method of claim 10 further including means whereby at any time on the user's demand the user may adjust parameters of the breath pacer pattern for better breathing technique compliance.

14. The method of claim 10 wherein said software further displays a session summary showing the results of the selected RSA training session.

15. The method of claim 10 wherein said software further displays a progress summary showing the results of the RSA training across all recorded sessions.

16. The method of claim 10 wherein said software further provides printed RSA training reports.

17. The method of claim 10 wherein said physiological monitoring device is an ECG.

18. The method of claim 10 wherein said physiological monitoring device is a PPG.

* * * * *